(12) United States Patent
Wang et al.

(10) Patent No.: US 12,371,740 B2
(45) Date of Patent: Jul. 29, 2025

(54) PRIMERS WITH SELF-COMPLEMENTARY SEQUENCES FOR MULTIPLE DISPLACEMENT AMPLIFICATION

(71) Applicant: QIAGEN SCIENCES, LLC, Germantown, MD (US)

(72) Inventors: Yexun Wang, Ellicott City, MD (US); Quan Peng, Clarksburg, MD (US)

(73) Assignee: QIAGEN Sciences, LLC, Germantown, MD (US)

( * ) Notice: Subject to any disclaimer, the term of this patent is extended or adjusted under 35 U.S.C. 154(b) by 210 days.

(21) Appl. No.: 17/849,078

(22) Filed: Jun. 24, 2022

(65) Prior Publication Data

US 2022/0364165 A1    Nov. 17, 2022

Related U.S. Application Data

(62) Division of application No. 16/088,001, filed as application No. PCT/US2017/023197 on Mar. 20, 2017, now Pat. No. 11,401,548.

(60) Provisional application No. 62/313,298, filed on Mar. 25, 2016.

(51) Int. Cl.
    *C12Q 1/6853* (2018.01)
(52) U.S. Cl.
    CPC .................. *C12Q 1/6853* (2013.01)
(58) Field of Classification Search
    None
    See application file for complete search history.

(56) References Cited

U.S. PATENT DOCUMENTS

| 6,617,137 B2 | 9/2003 | Dean et al. |
| 6,977,148 B2 | 12/2005 | Dean et al. |
| 7,074,600 B2 | 7/2006 | Dean et al. |
| 7,955,795 B2 | 6/2011 | Kumar |
| 8,497,069 B2 | 7/2013 | Hutchison, III et al. |
| 2005/0147975 A1 | 7/2005 | Schembri et al. |
| 2011/0189677 A1 | 8/2011 | Adli et al. |
| 2014/0213485 A1 | 7/2014 | Weissman et al. |
| 2016/0053253 A1 | 2/2016 | Salathia et al. |
| 2016/0304935 A1 | 10/2016 | Mir et al. |

FOREIGN PATENT DOCUMENTS

WO    2016/138080 A1    9/2016

OTHER PUBLICATIONS

Cheung et al., "Whole genome amplification using a degenerate oligonucleotide primer allows hundreds of genotypes to be performed on less than one nanogram of genomic DNA," *Proc. Natl. Acad. Sci. USA* 93:14676-14679 (Dec. 1996).
Dean et al., "Comprehensive human genome amplification using multiple displacement amplification," *Proc. Natl. Acad. Sci. USA* 99(8):5261-5266 (Apr. 16, 2002).
Dean et al., "Rapid Amplification of Plasmid and Phage DNA Using Phi29 DNA Polymerase and Multiply-Primed Rolling Circle Amplification," *Genome Research* 11:1095-1099 (2001).
Gawad et al., "Single-cell genome sequencing: current state of the science," *Nature Reviews, Genetics* 17:175-188 (Mar. 2016).
Motley et al., "Improved Multiple Displacement Amplification (iMDA) and Ultraclean Reagents," *BMC Genomics* 15:443 (10 pages) (2014).
REPLI-g® Single Cell Handbook, QIAGEN®, *Sample & Assay Technologies* (28 pages) (Oct. 2012).
QIAGEN Supplementary Protocol, "Whole genome amplification from genomic DNA using the REPLI-g® Single Cell Kit with increased sample volumes," QIAGEN®, *Sample & Assay Technologies* (4 pages) (2012).
Zhang et al., "Chromothripsis from DNA damage in micronuclei," *Nature* 522:179-184 (with Supplementary Information) (37 pages) (2015).
Zong et al., "Genome-Wide Detection of Single Nucleotide and Copy Number Variations of a Single Human Cell," *Science* 338(6114):1622-1626 (Dec. 21, 2012).

*Primary Examiner* — Samuel C Woolwine
*Assistant Examiner* — Carolyn L Greene
(74) *Attorney, Agent, or Firm* — Seed IP Law Group LLP

(57) ABSTRACT

The present disclosure provides primers, primer sets, kits and methods for multiple displacement amplification, especially in combination with nucleic acid sequencing. The primers comprise self-complementary sequences at their 5' termini and random or semi-random sequences at their 3' termini. Use of such primers facilitates handling of multiple samples, increases sequence coverage uniformity, and improves sequencing error corrections.

15 Claims, 2 Drawing Sheets
Specification includes a Sequence Listing.

SEQUENCE LISTING

<160> NUMBER OF SEQ ID NOS: 8

<210> SEQ ID NO 1
<211> LENGTH: 12
<212> TYPE: DNA
<213> ORGANISM: Artificial Sequence
<220> FEATURE:

```
<223> OTHER INFORMATION: Primer sequence

<400> SEQUENCE: 1
cgatcatgat cg                                                              12

<210> SEQ ID NO 2
<211> LENGTH: 18
<212> TYPE: DNA
<213> ORGANISM: Artificial Sequence
<220> FEATURE:
<223> OTHER INFORMATION: Primer sequence

<400> SEQUENCE: 2
cgatcacggc cgtgatcg                                                        18

<210> SEQ ID NO 3
<211> LENGTH: 12
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)...(12)
<223> OTHER INFORMATION: n = A,T,C or G

<400> SEQUENCE: 3
tgatcgnnnn nn                                                              12

<210> SEQ ID NO 4
<211> LENGTH: 16
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)...(16)
<223> OTHER INFORMATION: n = A,T,C or G

<400> SEQUENCE: 4
gccgtgatcg nnnnnn                                                          16

<210> SEQ ID NO 5
<211> LENGTH: 24
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)...(24)
<223> OTHER INFORMATION: n = A,T,C or G

<400> SEQUENCE: 5
cgatcacggc cgtgatcgnn nnnn                                                 24

<210> SEQ ID NO 6
<211> LENGTH: 18
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)...(18)
<223> OTHER INFORMATION: n = A,T,C or G

<400> SEQUENCE: 6
```

-continued

```
cgatcatgat cgnnnnnn                                                    18

<210> SEQ ID NO 7
<211> LENGTH: 16
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)...(16)
<223> OTHER INFORMATION: n = A,T,C or G

<400> SEQUENCE: 7
cgatcgatcg nnnnnn                                                      16

<210> SEQ ID NO 8
<211> LENGTH: 14
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)...(14)
<223> OTHER INFORMATION: n = A,T,C or G

<400> SEQUENCE: 8
cgatatcgnn nnnn                                                        14
```

PRIMERS WITH SELF-COMPLEMENTARY SEQUENCES FOR MULTIPLE DISPLACEMENT AMPLIFICATION

RELATED APPLICATION DATA

This application is a divisional application of U.S. application Ser. No. 16/088,001 filed Sep. 24, 2018, which is a 371 application of International Application No. PCT/US2017/023197 filed Mar. 20, 2017, which claims benefit of U.S. application Ser. No. 62/313,298 filed Mar. 25, 2016. U.S. application Ser. No. 16/088,001 is herein incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 830109_411D1_SEQUENCE_LISTING.txt. The text file is 2294 bytes, was created on Jun. 17, 2022, and is being submitted electronically via EFS-Web.

BACKGROUND

Technical Field

The present disclosure relates to primers, primer sets, kits and methods for multiple displacement amplification, especially in combination with nucleic acid sequencing.

Description of the Related Art

The advance of DNA sequencing technology enables genetic analysis of individual cells. Due to limited materials, genomic DNA from a single cell is usually amplified prior to sequencing preparation. However, Whole Genome Amplification (WGA) methods in general are prone to amplification bias, which results in low genome coverage. PCR-based WGA introduces sequence-dependent bias because of the exponential amplification with random primers. Multiple Displacement Amplification (MDA) using a DNA polymerase with a strand displacement activity under isothermal conditions has improved over PCR-based methods.

To maintain high amplification potency and to reduce bias, random sequences of 6-10 bases are usually used as primers in an MDA reaction. Each sample has to be processed individually because it is not possible to identify each sample until at a late stage of the procedure where a sample barcode is added to each reaction. This requirement limits throughput especially with a large number of samples, and substantially increases sample preparation costs.

Alternatively, regular MDA primers could be modified by adding defined sequences at their 5' termini. The region with a defined sequence can serve as a cell index sequence to distinguish DNA from different cells. After MDA, all samples with different cell indices could be immediately pooled and manipulated together for downstream sequencing preparation. Each sample could be identified later in sequencing reads by its cell index sequence. However, including cell index sequences in MDA primers increases amplification artefacts and bias.

BRIEF SUMMARY

The present disclosure provides primers, primer sets, kits and methods for multiple displacement amplification (MDA).

In one aspect, the present disclosure provides a method for amplifying nucleic acids by multiple displacement amplification, comprising:

performing one or more separate multiple displacement amplification reactions, wherein each reaction is performed in the presence of:
(1) a primer set, wherein each primer of the primer set comprises a self-complementary sequence at its 5' terminus and a random sequence or a semi-random sequence at its 3' terminus, and wherein the self-complementary sequences in each primer set are the same, but different from the self-complementary sequences in another primer set,
(2) a DNA polymerase having a strand displacement activity, and
(3) target nucleic acids.

In certain embodiments, the self-complementary sequences in one or more primer sets are each 6 to 20 nucleotides in length.

In certain embodiments, the random sequences or the semi-random sequences in one or more primer sets are 4 to 20 nucleotides in length.

Preferably, the primers are resistant to 3'→5' exonuclease proofreading activity.

In certain embodiments, the DNA polymerase having a strand displacement activity is Phi29 polymerase.

In certain embodiments, at least 2 separate multiple displacement amplification reactions are performed.

In certain embodiments, the target nucleic acids used in one or more separate multiple displacement amplification reactions are genomic DNA from one or more different single cells, such as human cells.

In certain embodiments, the multiple displacement amplification is performed at a temperature from about 20° C. to about 40° C., such as cycling between two temperatures within the above-noted range or under an isothermal condition.

In certain embodiments where a plurality of separate multiple displacement amplification reactions are performed, the method further comprises:
pooling the nucleic acids amplified from the plurality of multiple displacement amplification reactions together,
generating a sequencing library using the pooled amplified nucleic acids, and
sequencing the pooled amplified nucleic acids.

In another aspect, the present disclosure provides a primer set, wherein each primer in the primer set comprises a self-complementary sequence at its 5' terminus and a random sequence or a semi-random sequence at its 3' terminus, and wherein the self-complementary sequences of the primers are identical to each other.

In another aspect, the present disclosure provides a plurality of primer sets, wherein each primer comprises a self-complementary sequence at its 5' terminus and a random sequence or a semi-random sequence at its 3' terminus, wherein the self-complementary sequences of primers in each primer set are the same, but different from the self-complementary sequences of primers in another primer set.

In certain embodiments, the plurality of primer sets comprises at least 3 different primer sets.

In another aspect, the present disclosure provides a kit for amplifying nucleic acids using multiple displacement amplification, comprising:
(1) the primer set or the plurality of primer sets provided herein.
In certain embodiments, the kit further comprises:
(2) a DNA polymerase having a strand displacement activity.

In a related aspect, the present disclosure provides use of the primer set, the plurality of primer sets, or the kit provided herein for amplifying nucleic acids.

DETAILED DESCRIPTION

In the following description, any ranges provided herein include all the values in the ranges. It should also be noted that the term "or" is generally employed in its sense including "and/or" (i.e., to mean either one, both, or any combination thereof of the alternatives) unless the content dictates otherwise.

Also, as used in this specification and the appended claims, the singular forms "a," "an," and "the" include plural referents unless the content dictates otherwise. The terms "include," "have," "comprise" and their variants are used synonymously and to be construed as non-limiting. The term "about" refers to ±10% of a reference a value. For example, "about 30° C." refers to "30° C.±3° C." (i.e., 30° C.±10% of 30° C.).

The present disclosure provides primers, primer sets, kits and methods for multiple displacement amplification (MDA). The primers comprise self-complementary sequences at their 5' termini and random or semi-random sequences at their 3' termini. The self-complementary sequences may be used to label genomic DNA from individual cells while amplifying the genomic DNA. With minimized amplification bias and the ability of sample pooling immediately after MDA, the methods disclosed herein simplify sample preparation, especially when a large number of samples are analyzed, and reduce costs of sample preparation in high throughput sequencing workflow, such as in single cell sequencing workflow. In addition, the use of such primers in MDA reactions improves sequencing error corrections.

Figure 1:
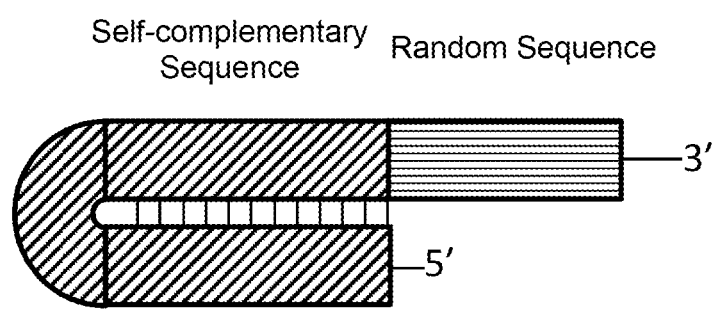
FIG. 1 is a schematic representation of an exemplary primer useful in an MDA reaction according to the present disclosure.
Figure 2:
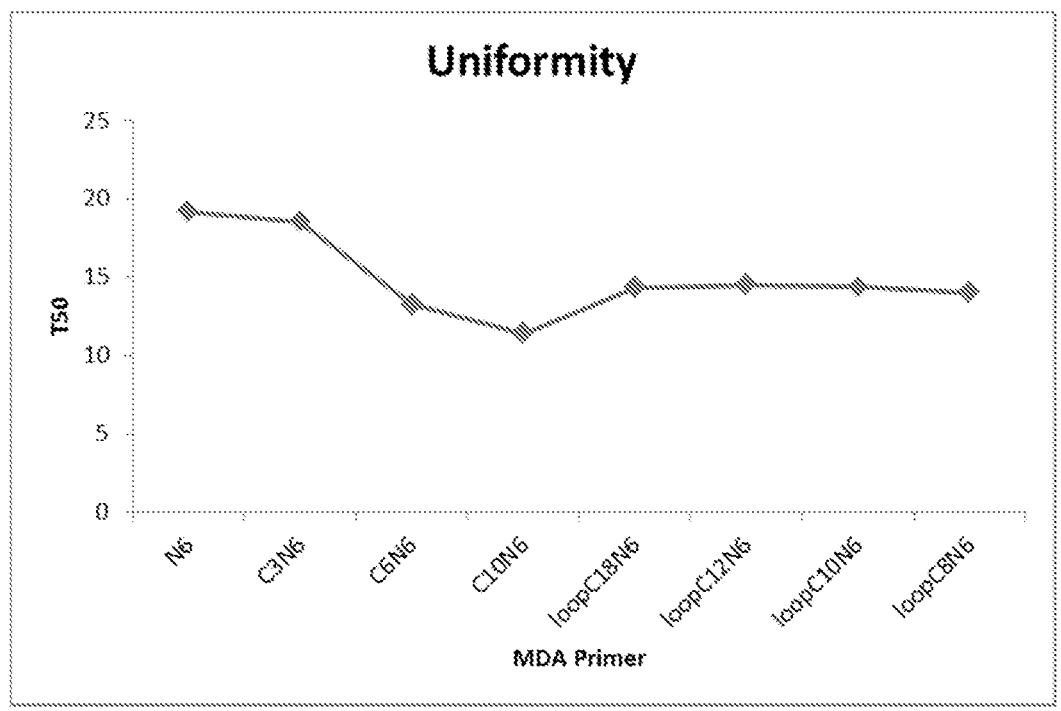
FIG. 2 is a graph showing sequence coverage uniformity (T50) of MDA reactions using various primers as described in the Example of the present disclosure.

A modification on an MDA primer that reduces randomness of the primer sequence, such as adding a defined sequence to be used as an index sequence at the 5' terminus of the primer, may introduce additional amplification bias (see e.g., the Example and FIG. 2). Without wishing to be bound by any theory, the present inventors believe that the bias is caused by the interaction between the defined sequence at the 5' terminus and the target DNA. To prevent this interaction, the present inventors made the defined sequence at the 5' terminus self-complementary and stabilized in stem-loop form, and observed significantly reduced impact on amplification uniformity by such a modification.

A. Multiple Displacement Amplification

In one aspect, the present disclosure provides a method for amplifying nucleic acids by multiple displacement amplification, comprising:
performing one or more separate multiple displacement amplification reactions, wherein each reaction is performed in the presence of:
(1) a primer set, wherein each primer of the primer set comprises a self-complementary sequence at its 5' terminus and a random sequence or a semi-random sequence at the 3' terminus, and wherein the self-complementary sequences in each primer set are the same, but different from the self-complementary sequences in another primer set,
(2) a DNA polymerase having a stand displacement activity, and
(3) target nucleic acids.

In certain embodiments, the method disclosed herein comprises performing one MDA reaction. In preferred embodiments, the method comprises performing two or more separate MDA reactions, preferably at least 3, 4, 5, 6, 7, 8, 9, 10, 20, 25, 30, 40, 50, 60, 70, 75, 80, 90, 100, 200, 300, 400, 500, 600, 700, 800, 900, or 1000 separate MDA reactions.

The term "Multiple Displacement Amplification (MDA)" as used herein refers to amplifying a linear target nucleic acid, such as genomic DNA, using a set of primers that are collectively complementary to nucleic acid sequences distributed throughout the target nucleic acid. Amplification proceeds by replication initiating at each primer and continuing so that the growing strands encounter and displace adjacent replicated strands.

As indicated above, the method for amplifying nucleic acids disclosed herein may comprise performing one MDA reaction. Such an MDA reaction uses a primer set wherein each primer of which comprises the same self-complementary sequence at its 5' terminus and a random sequence or a semi-random sequence at its 3' terminus. Thus, in a related aspect, the present disclosure provides a primer set useful for amplifying nucleic acids by MDA.

A "primer" is an oligonucleotide that comprises a sequence complementary to a target nucleic acid and leads to addition of nucleotides to the 3' end of the primer in the presence of a DNA polymerase using the target nucleic acid as a template.

An "oligonucleotide" refers to a short polymer composed of deoxyribonucleotides, ribonucleotides or combinations thereof. Oligonucleotides are generally between about 10 to about 100 nucleotides, preferably about 12 to about 60 nucleotides, in length.

The terms "complementary" and "complement" and their variants, as used herein, refer to any two nucleotide sequences that form a hybridized duplex by base pairing.

One nucleotide sequence may be completely complementary to another nucleotide sequence if all of the nucleotides in the sequence form base pairing with nucleotides in the corresponding antiparallel positions of the other sequence.

"Partial" complementarity describes nucleotide sequences in which at least 50%, but less than 100%, of the nucleotides of one sequence form base pairing with nucleotides in the corresponding antiparallel positions of the other sequence.

One nucleotide sequence is "substantially complementary" to another nucleotide sequence if the two sequences form a double-stranded like structure under conditions suitable for performing an MDA reaction. In certain embodiments, one nucleotide sequence substantially complementary to another nucleotide sequence has at least 80% (e.g., at least 85%, at least 90%, at least 95%, at least 98%, or at least 99%) nucleotides complementary to nucleotides in the corresponding antiparallel positions of the other sequence.

A "self-complementary sequence" refers to a nucleotide sequence comprises two sub-sequences that are substantially complementary to each other so that the nucleotide sequence folds back on itself, creating a double-stranded like structure due to base pairing between the two sub-sequences under conditions suitable for performing an MDA reaction. In some preferred embodiments, the two sub-sequences are completely complementary to each other. In certain other embodiments, the two sub-sequences are at least substantially complementary to each other. Exemplary self-complementary sequences include those disclosed in the Example below, such as CGATCATGATCG (SEQ ID NO: 1) in primer loopC12N6 and CGATCACGG<u>CCGTGATCG</u> (SEQ ID NO: 2) in primer loopC18N6 (the two sub-sequences in each primer are indicated in bold and by underline, respectively).

A "random sequence" refers to a nucleotide sequence where any one of the four nucleotides (i.e., A, T, G, and C) may be present at any position in the nucleotide sequence. For example, a random hexamer has a sequence of NNNNNN where "N" may be any of A, T, G, and C.

A "semi-random sequence" refers to a nucleotide sequence where (1) in at least one position ("semi-random position"), any one of two or three different nucleotides may be present, and/or (2) in at least one position ("random position"), any one of the four nucleotides (i.e., A, T, G, and C) may be present and in at least another position, a defined nucleotide is present. For example, the sequence DDDDDD where "D" may be any of A, T and G is a semi-random sequence, which comprises 6 semi-random positions (i.e., where "D" is located). The sequence NNANNA where "N" may be any of A, T, G, and C is also a semi-random sequence, which comprises 4 random positions (i.e., where "N" is located) and 2 positions with a defined nucleotide (i.e., A). The sequence NNDNND is another type of semi-random sequences that consist of both semi-random positions and random positions. The sequence NDANDA is yet another type of semi-random sequences that comprise semi-random positions, random positions, and one or more positions with defined nucleotide(s).

The primer useful for amplifying nucleic acids by MDA may have the following structure:

5'-S-L-S'-Z-R-3'

S and S' are two sub-sequences that are substantially, preferably completely, complementary to each other in the antiparallel orientation, so that the primer folds back on itself and S and S' together form the "stem" portion of the primer. The self-complementary of the primer due to sub-sequences S and S' prevents the region ("the self-complementary sequence") consisting of S, L, and S' from annealing to a target nucleic acid. S and S' preferably have the same number of nucleotides. They may each have 2, 3, 4, 5, 6, 7, 8, 9, 10, 11, 12, 13, 14, 15, 16, 17, 18, 19, or 20 nucleotides, including any ranges between two of the above-listed numbers, such as 3 to 9 nucleotides or 3 to 6 nucleotides.

L is an optional sequence between sub-sequences S and S'. Preferably, it is absent from the primer sequence. However, in certain embodiments, L may be 1, 2, or 3 nucleotides long. In such embodiments, the term "self-complementary sequence" includes 5'-S-L-S'-3'.

The self-complementary sequence may have 4, 5, 6, 7, 8, 9, 10, 11, 12, 13, 14, 15, 16, 17, 18, 19, 20, 21, 22, 23, 24, 25, 26, 27, 28, 29 or 30 nucleotides, including any ranges between two of the above-listed numbers, such as 6 to 18 nucleotides or 6 to 12 nucleotides.

R is a random sequence or a semi-random sequence, which may be 4, 5, 6, 7, 8, 9, 10, 11, 12, 13, 14, 15, 16, 17, 18, 19, 20, or more nucleotides long. Preferably, R is 6, 7, 8, 9 or 10 nucleotides long.

Z is an optional sequence between subsequences S' and R. Preferably, Z is absent from the primer sequence. However, in certain embodiments, Z may be 1, 2, or 3 nucleotides long.

The total length of the primer may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides, including any ranges between two of the above-listed numbers, such as 12 to 24 nucleotides or 10 to 30 nucleotides.

Preferably, the primer includes one or more modified nucleotides to render it resistant to 3'→5' exonuclease digestion. For example, 1, 2, 3 or more phosphorothioate linkages may be present. In certain embodiments, the two most 3' terminal nucleotides are linked by phosphorothioate linkages; or the three most 3' terminal residues are so linked. In certain other embodiments, all of the nucleotides in the random or semi-random sequence are linked by phosphorothioate linkages.

In each MDA reaction, the total concentration of a primer set may range from about 1 nM to about 1 mM, such as about 1 nm to about 1 µM, about 1 µM to 1 mM, about 1 nM to about 100 nM, about 100 nM to about 10 µM, about 10 µM to about 1 mM, about 1 µM to about 500 µM, about 1 µM to about 200 µM, about 1 µM to about 100 µM, about 25 µM to about 75 µM, and about 40 µM to 60 µM. In certain embodiments, the total concentration of a primer set in an MDA reaction is about 50 µM.

The number of primers in a primer set largely depends on the number of semi-random positions (if any) and random positions (if any) in the primer sequences. For example, a prime set of primers having a random hexamer have about $4^6$ different primers. A primer set of primers having a semi-random primer have about $2^x 3^y 4^z$ different primers wherein x, y, and z are the numbers of positions at which one out of 2 nucleotides, one out of 3 nucleotides, or one out of 4 nucleotides may be present, respectively.

In certain embodiments, a semi-random sequence may have 2, 3, 4, 5, 6, 7, 8, 9, 10, 11, 12, 13, 14, 15, 16, 17, 18, 19, 20, or more random positions. In certain embodiments, a semi-random sequence may have 2, 3, 4, 5, 6, 7, 8, 9, 10, 11, 12, 13, 14, 15, 16, 17, 18, 19, 20, or more semi-random positions (at which positions one out of 2 nucleotides or one out of 3 nucleotides may be present). In certain embodiments, a semi-random sequence may have 2, 3, 4, 5, 6, 7, 8, 9, 10, 11, 12, 13, 14, 15, 16, 17, 18, 19, 20, or more random positions. In certain other embodiments, a semi-random sequence may independently have 2, 3, 4, 5, 6, 7, 8, 9, 10, 11, 12, 13, 14, 15, 16, 17, 18, 19, 20, or more semi-random positions and 2, 3, 4, 5, 6, 7, 8, 9, 10, 11, 12, 13, 14, 15, 16, 17, 18, 19, 20, or more random positions. "Independently" as used above means that the number of semi-random positions in a semi-random sequence may be chosen independently from the number of random positions in the semi-random sequence.

In preferred embodiments, the method for amplifying nucleic acids disclosed herein comprises performing multiple separate MDA reactions using different primer sets. Thus, in a related aspect, the present disclosure provides a plurality of primer sets useful for amplifying nucleic acids.

In the plurality of primer sets, each primer comprises a self-complementary sequence at its 5' terminus and a random sequence or a semi-random sequence at its 3' terminus as described above. In addition, the self-complementary sequences of primers in each primer set are the same, but different from the self-complementary sequences of primers in another primer set. In certain embodiments, the random sequences or semi-random sequences of the primers in the plurality of primer sets have the same number of nucleotides. In certain other embodiments, the random sequences or semi-random sequences of the primers in the plurality of primer sets have different numbers of nucleotides.

The plurality of primer sets may comprise at least 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 350, 400, 450, 500, 600, 700, 800, 900, or 1000 different primer sets.

Different self-complementary sequences in primers of different primer sets are used as indices for identifying target nucleic acids from different samples and thus allowing amplification products from separate MDA reactions to be pooled together for subsequent analysis. For example, genomic DNA from different single cells may be used as templates in separate MDA reactions that use primers with different self-complementary sequences. The amplification products of the separate MDA reactions may then be pooled together and sequenced. Based on the identities of self-complementary sequences, the sources of genomic DNA that have been amplified may be determined. The self-complementary sequences used in single cell sequencing are referred to herein as "cell index sequences."

DNA polymerases useful in MDA are capable of displacing, either alone or in combination with a compatible strand displacement factor, a hybridized strand encountered during replication.

It is preferred that a DNA polymerase lacks a 5' to 3' exonuclease activity. Strand displacement is necessary to synthesize multiple copies of a target sequence. A 5' to 3' exonuclease activity, if present, may degrade a synthesized strand.

It is also preferred that DNA polymerases are highly processive. The term "processive," as used herein, means that the DNA polymerase remains attached to the elongation complex without dissociating, thereby allowing the elongation of very long DNAs.

It is also preferred that DNA polymerases have high fidelity and low error rates. Use of such DNA polymerases reduces amplification artefacts.

It is further preferred that DNA polymerases are active at a relatively low temperature, such as 20° C. to 50° C., 25° C. to 45° C. or 28° C. to 35° C. Such DNA polymerases will allow MDA performed at the relative low temperature so that the self-complementary sequences of the primers used in MDA remain in their looped stem form and are unable to anneal to target nucleic acids to reduce the randomness of the primers.

Any DNA polymerase that is 5'→3' exonuclease deficient but preferably has a strand displacement activity may be used in the methods of the present disclosure. Such DNA polymerases include, but are not limited to, exo-Deep Vent, exo-Bst, exo-Pfu, and exo-Bca.

Additional exemplary DNA polymerases useful in the present invention include, but are not limited to, phage M2 DNA polymerase (Matsumoto et al., Gene 84: 247, 1989), phage PhiPRD1 DNA polymerase (Jung et al., Proc. Natl. Acad. Sci. USA 84: 8287, 1987), T5 DNA polymerase (Chatterjee et al., Gene 97: 13-19, 1991), Sequenase (U.S. Biochemicals), PRD1 DNA polymerase (Zhu and Ito, Biochim. Biophys. Acta. 1219: 267-76, 1994), 9° Nm™ DNA polymerase (New England Biolabs) (Southworth et al., Proc. Natl. Acad. Sci. 93: 5281-5, 1996; Rodriquez et al., J. Mol. Biol. 302: 447-62, 2000), and T4 DNA polymerase holoenzyme (Kaboord and Benkovic, Curr. Biol. 5: 149-57, 1995).

Preferably, the DNA polymerase is phi29 polymerase (also referred to as Φ29 Pol; Φ29 polymerase; or phi29 DNA polymerase or the like) (see e.g., U.S. Pat. Nos. 5,198,543 and 5,001,050). Purified phi29 polymerase is available commercially, e.g., from New England Biolabs. Phi29 polymerase has been shown to amplify circular DNA isothermally at 30° C., by a highly processive rolling circle mechanism (Lizardi et al., Nat Genet. 19: 225-32, 1998; Dean et al., Genome Res. 11: 1095-9, 2001). Phi29 polymerase has a 3'→5' exonuclease proofreading activity and has been reported to have an error rate of only 1 in $10^6$-$10^7$ bases and exhibit a much higher fidelity than the polymerases used for PCR (Esteban et al., J Biol Chem 268: 2719-26, 1993).

If necessary, strand displacement can be facilitated through the use of a strand displacement factor, such as helicase. It is considered that any DNA polymerase that can perform MDA in the presence of a strand displacement factor is suitable for use in the disclosed method, even if the DNA polymerase does not perform MDA in the absence of such a factor.

In certain embodiments, the amplification is performed in the presence of a strand displacement facilitator. Exemplary strand displacement facilitators include, but are not limited to, helicase, BMRF1 polymerase accessory subunit, adenovirus DNA-binding protein, herpes simplex viral protein ICP8, single-stranded DNA binding proteins, phage T4 gene 32 protein, calf thymus helicase, and trehalose. In certain preferred embodiments, the stand displacement facilitator is trehalose or phage T4 gene 32 protein.

The ability of a polymerase to carry out MDA may be determined by using the polymerase in a conventional assay, such as the methods in Fire et al., Proc. Natl. Acad. Sci. USA 92, 4641-4645, 1995, U.S. Pat. No. 5,631,147, International Application No. WO 03/033724, and Kong et al., J. Biol. Chem. 268: 1965-1975, 1993, which may be modified as appropriate.

The concentration or amount of a DNA polymerase in an MDA reaction may vary depending on the particular DNA polymerase. In any case, the concentration or amount of the DNA polymerase has to be sufficient to generate a desired number or amount of amplified nucleic acids. In certain embodiments where phi29 polymerase is used, its concentration may range from about 100 units/ml to about 1500 units/ml, such as from about 500 units/ml to about 1000 units/ml.

A nucleic acid sample that contains target nucleic acids to be amplified may be prepared from any samples that contain nucleic acids of interest. Exemplary samples include, but are not limited to, samples from a human, animal, plant, bacterium, or fungus, including blood, plasma and serum, dried blood spots, swabs (e.g., buccal swabs), flash-frozen tissue, laser-microdissected cells, biopsies, body fluid, liver, spleen, kidney, lung, intestine, brain, heart, muscle, pancreas, cell cultures, leaves, stems, flowers, roots, as well as lysates, extracts, or materials and fractions obtained from the samples described above, or any cells, microorganisms and viruses that may be present on or in the samples described above, and the like. A nucleic acid sample may also be prepared from processed samples including preserved, fixed and/or stabilized samples, such as formalin fixed and paraffin-embedded (FFPE samples) and other samples that were treated with cross-linking fixatives such as glutaraldehyde.

Nucleic acids may be isolated from a sample of interest to obtain a nucleic acid sample by any method known in the art useful for nucleic acid isolation or purification. In addition, many kits for nucleic acid preparation are commercially available and may be used, including QIAamp DNA mini kit, QIAamp FFPE Tissue kit, and PAXgene DNA kit.

Any nucleic acids of interest may be amplified according to the method provided herein. Nucleic acids particularly of interest are those from dried blood spots, buccal cells, laser-microdissected cells, biopsies, plasma and serum, and flash-frozen tissue.

In certain embodiments, the method of amplifying nucleic acids using MDA is amplification of a whole target genome. As used herein, "whole genome" (or "target genome") refers to at least 80% (e.g., at least 85%, 90%, 95%, 98% or 99%) of the total set of genes and nucleic acid sequences between these genes carried by an organism, a cell or an organelle.

As used herein, "whole genome amplification" refers to the making of multiple nucleic acid molecules using a whole target genome as a template. These nucleic acid molecules each must comprise a nucleotide sequence identical to a portion of the target genome. Typically, these nucleic acid molecules, in combination, comprise the majority portion of the sequence (i.e., at least 51%) of the target genome. Preferably, such nucleic acid molecules, in combination, comprise 60%, 70%, 80%, 90%, 95%, or 100% of the target genome.

In embodiments where the method of the present disclosure is used to amplify a whole target genome, a sufficiently large set of primers comprising random or semi-random sequences will be collectively, and randomly, complementary to nucleic acid sequences distributed throughout the whole target genome in the sample. Amplification proceeds by replication with a processive DNA polymerase initiated at each primer and continuing until spontaneous termination. A key feature of this method is the displacement of intervening primers during replication by the polymerase. In this way, multiple overlapping copies of the entire genome can be synthesized in a short time.

In certain embodiments for whole genome amplification, preferred nucleic acid samples are nucleic acid samples from a single cell. Where the nucleic acid sample is a genomic nucleic acid sample, the genome can be the genome from any organism of interest. For example, the genome can be a viral genome, a bacterial genome, a eubacterial genome, an archae bacterial genome, a fungal genome, a microbial genome, a eukaryotic genome, a plant genome, an animal genome, a vertebrate genome, an invertebrate genome, an insect genome, a mammalian genome, or a human genome.

For whole genome amplification using samples of single cells or a small number of cells, the preparation of target nucleic acids may be carried out according to various methods known in the art (see e.g., Dean et al., PNAS 99: 5261-6, 2002, Qiagen's REPLI-g Single Cell Handbook October 2012). Briefly, the cell sample is lysed and the DNA in the sample is denatured. After denaturation has been stopped by the addition of neutralization buffer, an MDA reaction may then be performed in the presence of a primer set and a DNA polymerase as disclosed herein. Alternatively, purified genomic DNA may be first denatured. Again, after a neutralization buffer is added to stop denaturation, a mixture comprising a primer set and a DNA polymerase may be added for carrying out an MDA reaction.

The amount of target nucleic acids used as templates in an MDA reaction may range from about 0.001 ng to about 500 ng, such as from about 0.03 ng to about 300 ng, or from about 0.1 ng to about 100 ng.

In addition to target nucleic acids, a DNA polymerase, a primer set, an MDA reaction mixture may also contain one of the following additional components:

a buffer (e.g., Tris HCl, pH 7.5 at a concentration ranging, for example, from about 10 mM to about 50 mM, such as about 37 mM), $Mg^{2+}$, such as $MgCl_2$ at a concentration ranging, for example, from about 1 mM to about 50 mM, such as about 10 mM, $(NH_4)_2SO_4$ at a concentration ranging, for example, from about 1 mM to about 10 mM, such as about 5 mM, and dNTPs at a concentration ranging, for example, from about 1 mM to about 10 mM, such as about 5 mM.

One or more of the following components may also be included in an MDA reaction mixture:

KCl at a concentration ranging, for example, from about 10 mM to about 100 mM, such as about 50 mM, a strand displacement factor, such as trehalose dehydrate at a concentration ranging, for example, from about 0.3 M to about 1 M, such as about 0.57M, a detergent, such as Tween 40 at a concentration ranging, for example, from about 0.2% v.v to about 5% v/v, such as about 1.1% v/v, a reducing agent, such as dithiothreitol (DTT) at a concentration ranging, for example, from about 1 mM to about 10 mM, such as about 4 mM.

MDA reactions according to the present disclosure may be performed isothermally, that is, at a fixed temperature or within a narrow temperature range that is no more than about 6° C., such as no more than about 5° C., no more than about 4° C., no more than about 3° C., or no more than about 2° C.

Alternatively, MDA reactions according to the present disclosure may also be performed by cycling between two temperatures, such as between any two temperatures within the range of about 20° C. to about 50° C.

The temperature under which an MDA reaction is performed varies depending on the DNA polymerase and/or the primer set. The temperature should be appropriate for the DNA polymerase so that the DNA polymerase is active under such a temperature. In addition, the temperature should not be too high to cause the sub-sequences of the self-complementary sequence in the primers to separate from each other and thus become available to base pair with target nucleic acids. Furthermore, the temperature should not be too high to prevent the random or semi-random sequence of the primers from base pairing with target nucleic acids.

In certain embodiments wherein phi29 polymerase is used in an MDA reaction, the reaction may be performed at a temperature at about 28° C. to 33° C., such as at about 30° C., 31° C. or 32° C.

In certain embodiments, MDA reactions are performed at about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50° C. or by cycling between two of the above-listed temperatures, such as from about 20° C. to about 50° C., from about 20° C. to about 0° C., from about 20° C. to about 30° C., or from about 25° C. to about 35° C.

MDA reactions as disclosed herein are carried out for a sufficient time to produce a sufficient amount of amplification products for downstream analysis, such as sequencing analysis. They may be performed for about 1, 2, 3, 4, 5, 6, 7, 8, 9, 10 or more hours.

The amplification products of each MDA reaction carry a specific self-complementary sequence at their 5' termini. Because different reactions using primers having different self-complementary sequences, in downstream applications, such as next generation sequencing (NGS) applications, all samples with different self-complementary sequences can be combined and manipulated together. The self-complementary sequences thus function as index sequences that allow tracing a sequence obtained by NGS to the sample from which the sequence is derived.

In certain embodiments, the methods disclosed herein further comprise one or more of the following steps:
  if multiple separate MDA reactions are performed, pooling the nucleic acids amplified from the plurality of MDA reactions together,
  generating a sequencing library using the amplified nucleic acids from a single MDA reaction or the pooled amplified nucleic acids from multiple separated MDA reactions, and sequencing the amplified nucleic acids or the pooled amplified nucleic acids.

The amplification products of an MDA reaction or the amplification products pooled from multiple separate MDA reactions may be directly used to ligate to one or more adapters. Alternatively, they may first be modified, such as by adding adenines to their 3' ends to facilitate ligation to one or more adapters having a T overhang.

Methods for ligating adapters to blunt-ended nucleic acids are known in the art and may be used in generating sequencing libraries from amplification products of PCR as provided herein. Exemplary methods include those described in Sambrook J and Russell DW, editors. (2001) Molecular Cloning: A Laboratory Manual. 3rd ed. Cold Spring Harbor, NY: Cold Spring Harbor Laboratory, QIAGEN GENEREAD™ Library Prep (L) Handbook and U.S. Patent Application Publication Nos. 2010/0197509, 2013/0005613.

Similarly, methods for ligating adapters having a T overhang with modified amplification products having adenines added to their 3' ends are also known in the art (see, e.g., QIAGEN GENEREAD™ Library Prep (I) Handbook).

The adapters ligated to the two ends of a blunt-ended nucleic acid may be the same or different. Preferably, they are different. In certain embodiments, one of the two adapters may carry a group (e.g., a biotin group) to facilitate the isolation of adapted nucleic acids having two different adapters. For example, two adapters, "A" and "B," are ligated to the ends of nucleic acids. Adapter "B" carries a biotin group, which facilitates the purification of homoadapted nucleic acids (A/A or B/B). The biotin labeled sequencing library is captured on streptavidin beads. Nucleic acids containing the biotin labeled B adapter are bound to the streptavidin beads while homozygous, nonbiotinylated A/A adapters are washed away. The immobilized nucleic acids are denatured after which both strands of the B/B adapted nucleic acids remain immobilized by the streptavidin-biotin bond and single-strand template of the A/B nucleic acids are freed and used in sequencing.

The resulting sequencing library may be first amplified before being sequenced. Amplification of the sequencing library may be performed in situ, in emulsion or in solution, including bridge PCR (see e.g., U.S. Pat. No. 5,641,658) and emulsion PCR (see e.g., Williams et al., Nature Methods 3:545-50, 2006). Alternatively, the sequence library may directly be sequenced without amplification.

Sequencing the DNA molecules in the sequencing library or libraries may be carried out in known sequencing methods, preferably those using high throughput sequencing platforms (see e.g., Myllykangas et al., *Bioinformatics for High Throughput Sequencing*, Rodriguez-Ezpeleta et al. (eds.), Springer Science+Business Media, LLC, 2012, pages 11-25). Exemplary high throughput DNA sequencing systems include, but are not limited to, the GS FLX sequencing system originally developed by 454 Life Sciences and later acquired by Roche (Basel, Switzerland), Genome Analyzer developed by Solexa and later acquired by Illumina Inc. (San Diego, CA) (see, Bentley, Curr Opin Genet Dev 16:545-52, 2006; Bentley et al., Nature 456:53-59, 2008), the SOLiD sequence system by Life Technologies (Foster City, CA) (see, Smith et al., Nucleic Acid Res 38: e142, 2010; Valouev et al., Genome Res 18:1051-63, 2008), CGA developed by Complete Genomics and acquired by BGI (see, Drmanac et al., Science 327:78-81, 2010), PacBio RS sequencing technology developed by Pacific Biosciences (Menlo Park, CA) (see, Eid et al., Science 323: 133-8, 2009), and Ion Torrent developed by Life Technologies Corporation (see, U.S. Patent Application Publication Nos. 2009/0026082; 2010/0137143; and 2010/0282617).

During data analysis, certain errors in the self-complementary sequences in sequence reads may be corrected. Such errors could be identified and corrected because they are likely to render the sequences no longer self-complementary in most cases. For example, if a self-complementary sequence consists of subsequences S and S' but a sequence read contains the same sequence as S but one nucleotide difference from S', it is likely that the nucleotide difference is due to an amplification or sequencing error and should be corrected according to the sequence of S'.

As disclosed above, making 5' index sequences of MDA primers self-complementary minimizes the adverse impact on amplification uniformity by including the index sequences in MDA primers. Thus, when the MDA amplification products are used in sequencing reactions, the sequence coverage uniformity of such reactions is also improved over the sequence coverage uniformity where index sequences in MDA primers are not self-complementary.

Sequence coverage uniformity may be measured by T50, the percentage of total sequence throughput captured by the bottom 50% of a target region. In the perfect uniform scenario, the T50 value equals to 50.

In certain embodiments, the sequence coverage uniformity (T50) of sequencing the amplification products pooled from multiple MDA reactions pooled together according to the methods disclosed herein is at least about 10, 11, 12, 13, 14, or 15.

The methods disclosed herein are useful in amplifying any nucleic acids of interest, especially in amplifying nucleic acids from a large number of samples. In addition, in the embodiments where MDA reactions are combined with downstream NGS, the methods of the present disclosure are particularly useful in genomic analysis of nucleic acids from single cells (i.e., single cell sequencing) or limited sample materials. Such analysis facilitates identification of point mutations and/or chromosome rearrangements occurred in diseases, such as cancer. Additional applications of the methods disclosed herein include epigenetic studies, genetic pathogen diversity analysis, and in the areas of paleogenomics, forensics, and human genetics to analyze subpopulations in complex biological samples. Clinical applications include prenatal screening for fetal aneuploidy, early detection of cancer, monitoring patients' response to therapy, and predicting treatment efficacy in individual patients.

In another aspect, the present disclosure provides a kit for amplifying nucleic acids using MDA, comprising the primer set or a plurality of primer sets as described above in connection of methods for amplifying nucleic acids.

In certain embodiments, the kit may further comprise one or more of the following components for carrying out an MDA reaction:
DNA polymerase suitable for performing an MDA reaction, and
a reaction mixture that comprises dNTPs, a buffer substance, $Mg^{2+}$, $(NH_4)_2SO_4$, and optionally a strand displacement facilitating factor (e.g., trehalose dehydrate), a detergent, and/or a reducing agent.

In certain embodiments, the kit may further comprise one or more components for generating sequencing libraries, amplifying sequencing libraries, and/or performing NGS, such as a DNA polymerase for performing PCR, a PCR reaction buffer, a ligase, a ligation buffer, and one or more sequencing primers.

In a related aspect, the present disclosure provides use of the kits, primers, primer sets for amplifying nucleic acids using MDA and optionally sequencing the amplified nucleic acids, especially whole genome sequencing from single cells.

The following example is for illustration and are not limiting.

EXAMPLE

Amplification Uniformity Using Primers with Different Cell Indices

In this example, the following primers with different cell indices (i.e., the defined sequences 5' to the random hexamer sequence as shown below) were used in MDA reactions:

N6 (random hexamer: NNNNNN),

C3N6 (3nt cell index + N6: TCGNNNNNN), (SEQ ID NO: 3)
C6N6 (6nt cell index + N6: TGATCGNNNNNN), (SEQ ID NO: 4)
C10N6 (10nt cell index + N6: GCCGTGATCGNNNNNN), (SEQ ID NO: 5)
loopC18N6 (18nt cell index forming stem loop structure + N6: CGATCACGGCCGTGATCGNNNNNN, (SEQ ID NO: 6)
loopC12N6 (12nt cell index forming stem loop structure + N6: CGATCATGATCGNNNNNN), (SEQ ID NO: 7)
loopC10N6 (10nt cell index forming stem loop structure + N6: CGATCGATCGNNNNNN),
and (SEQ ID NO: 8)
loopC8N6 (8nt cell index forming stem loop structure + N6: CGATATCGNNNNNN).

In each MDA reaction, 10 ng of human genomic DNA was prepared according to manufacturer's recommendation in QIAGEN's REPLI-g Single Cell Kit, except that the kit-supplied MDA primer was substituted by the above primers respectively. Reactions were incubated at 30° C. for 16 hrs.

To evaluate amplification uniformity (T50), targeted sequencing on 140kb regions throughout human genome was performed. Briefly, MDA amplified DNA was purified using Agencourt AMPure XP beads (Beckman Coulter, Inc.). 500 ng of each DNA was then subjected to sequencing library construction (End repair, A-addition and Adapter ligation) according to manufacturer's recommendation in QIAGEN's GeneRead DNA Library Prep I Kit. A primer pool containing 1319 different primers was used to amplify and enrich the 140kb regions. The final libraries were then sequenced on Illumina's MiSeq. Sequence data were processed and T50 value was calculated The results (FIG. 2) show that a longer cell index sequence in a normal linear structure significantly reduced the sequence coverage uniformity of MDA (comparing T50 values among primers C3N6, C6N6, and C10N6). Without wishing to be bound by any theory, the present inventors believe that cell index sequences in a linear structure interacted with genomic DNA and thus reduced the randomness of N6 hybridization with target nucleic acids. The longer the cell index sequence in a linear structure, the severer the bias in amplification, thus the lower the sequence coverage uniformity. The loop structures of cell index sequences prevented these sequences from interacting with genomic DNA, and thus increased randomness of primer hybridization with target nucleic acids. Even with cell index length of 18 nt in a looped structure, the sequence coverage uniformity was greatly improved compared to those with much shorter normal cell index primers (e.g., primers C6N6 and C10N6). Changing the cell index sequence length in a looped structure had little effect on sequence coverage uniformity, as long as this region was protected (i.e., self-complementary).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A plurality of primer sets, wherein each primer comprises a self-complementary sequence at its 5' terminus and a random sequence or a semi-random sequence at its 3' terminus, wherein the self-complementary sequences of primers in each primer set are the same, but different from the self-complementary sequences of primers in another primer set.

2. The plurality of primer sets of claim 1, comprising at least 3 different primer sets.

3. A kit for amplifying nucleic acids using multiple displacement amplification,
comprising: the plurality of primer sets of claim 2.

4. The kit of claim 3, further
comprising: a DNA polymerase having a strand displacement activity.

5. The kit of claim 4, wherein the DNA polymerase having a strand displacement activity is Phi29 polymerase.

6. The kit of claim 3, wherein each primer of the plurality of primer sets has the following structure:

5'-S-L-S'-Z-R-3' wherein
(i) S-L-S' is the self-complementary sequence, wherein S and S' are two sub-sequences that are substantially complementary to each other, and
L is an optional sequence between sub-sequences S and S',
(ii) Z is an option sequence between sub-sequences S' and R, and
(iii) R is the random sequence or the semi-random sequence.

7. The kit of claim 6, wherein Z is absent.

8. The kit of claim 3, wherein each primer comprises a random sequence at its 3' terminus.

9. The kit of claim 3, wherein the self-complementary sequences in the primers of the plurality of primer sets are each 6 to 20 nucleotides in length.

10. The kit of claim 3, wherein the random sequences or the semi-random sequences in the primers of the plurality of primer sets are 4 to 20 nucleotides in length.

11. The plurality of primer sets of claim 1, wherein each primer of the plurality of primer sets has the following structure:

5'-S-L-S'-Z-R-3' wherein
(i) S-L-S' is the self-complementary sequence, wherein S and S' are two sub-sequences that are substantially complementary to each other, and
L is an optional sequence between sub-sequences S and S',
(ii) Z is an optional sequence between sub-sequences S' and R, and
(iii) R is the random sequence or the semi-random sequence.

12. The plurality of primer sets of claim 11, wherein Z is absent.

13. The plurality of primer sets of claim 1, wherein each primer comprises a random sequence at its 3' terminus.

14. The plurality of primer sets of claim 1, wherein the self-complementary sequences in the primers of the plurality of primer sets are each 6 to 20 nucleotides in length.

15. The plurality of primer sets of claim 1, wherein the random sequences or the semi-random sequences in the primers of the primer sets are each 4 to 20 nucleotides in length.

* * * * *

UNITED STATES PATENT AND TRADEMARK OFFICE
CERTIFICATE OF CORRECTION

| | |
|---|---|
| PATENT NO. | : 12,371,740 B2 |
| APPLICATION NO. | : 17/849078 |
| DATED | : July 29, 2025 |
| INVENTOR(S) | : Yexun Wang et al. |

Page 1 of 1

It is certified that error appears in the above-identified patent and that said Letters Patent is hereby corrected as shown below:

In the Claims

Column 17, Claim 3, Line 45:
"claim 2" should read: --claim 1--.

Signed and Sealed this
Fourteenth Day of October, 2025

John A. Squires
*Director of the United States Patent and Trademark Office*